United States Patent
Suck et al.

(10) Patent No.: US 8,329,185 B2
(45) Date of Patent: Dec. 11, 2012

(54) METHOD FOR ISOLATING AND PURIFYING GRASS POLLEN ALLERGENS

(75) Inventors: Roland Suck, Hamburg (DE); Oliver Cromwell, Wantorf (DE); Helmut Fiebig, Schwarzenbek (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 12/000,507

(22) Filed: Dec. 13, 2007

(65) Prior Publication Data

US 2008/0118536 A1   May 22, 2008

Related U.S. Application Data

(62) Division of application No. 10/069,285, filed on Aug. 8, 2002, now Pat. No. 7,326,769.

(30) Foreign Application Priority Data

Aug. 24, 1999  (DE) .................................. 199 39 382

(51) Int. Cl.
| | | |
|---|---|---|
| A61K 39/00 | (2006.01) | |
| A61K 39/38 | (2006.01) | |
| A61K 39/35 | (2006.01) | |
| A61K 39/36 | (2006.01) | |
| C07K 1/00 | (2006.01) | |
| C07K 14/00 | (2006.01) | |
| C07K 17/00 | (2006.01) | |

(52) U.S. Cl. .................... 424/184.1; 424/275.1; 530/350
(58) Field of Classification Search .......................... None
See application file for complete search history.

(56) References Cited

U.S. PATENT DOCUMENTS 6,277,383 B1   8/2001   Singh et al.

FOREIGN PATENT DOCUMENTS

WO      WO 0065060      11/2000

OTHER PUBLICATIONS https://www.allergen.org/Allergen.aspx.*
Westritschnig et al. 'Different allergenic activity of grass pollen allergens revealed by skin testing.' Eur. J. Clin. Invest. 38(4):260-267, 2008.*
Tarzi et al. 'Peptide immunotherapy for allergic disease.' Expert Opin. Biol. Therapy. 3(4):617-626, 2003.*
Vrtala et al. 'Immunization with purified natural and recombinant allergens induces mouse IgG1 antibodies that recognize similar epitopes as human IgE and inhibit the human IgE-allergen interaction and allergen-induced basophil degranulation.' J. Immunol. 160:6137-6144, 1998.*
Ferreira et al., FASEB J. 12:231-242, 1998, abstract only.*
Smith et al., Clin. and Exp. Allergy, 27:593-599, 1997, abstract only.*
Spangfort et al., Int. Arch. Allery Immunol., 119:243-245, 1997, abstract only.*
Sparholt et al, Clinical and Experimental Allergy; 27:932-941, 1997, abstract only.*
Aki et al., Int. Arch. Allergy. Immunol. 103:357-364, 1994, abstract only.*
Burks et al., Eur J. Biochem, 245:334-339, 1997, abstract only.*
Gajhede et al., Nature Structural Biology. 3(12): 1040-1045, 1996, abstract only.*
Lu et al., J. of Immunology. 150(7):2823-2830, 1993, abstract only.*
Ipsen et al., Clinical and Experimental Allergy. 22:391-399, 1992, abstract only.*
Ferreira et al., Advances in Experimental Medicine and Biology. 409:127-135, 1996, abstract only.*
Faber C. et al., The Journal of Biological Chemistry. 271(32):19243-19250, 1996, abstract only.*
Fernandez Rivas et al., Allergol Immunopathol (Madr). 31 (3): 141-6, 2003, abstract only.*
Petersen et al., J. Allergy Clin. Immunol. 107(5): 856-862, 2001, abstract only.*
Aalberse et al., J Allergy Clin Immunol. 106(2):228-38, 2000, abstract only.*
De Marino Set al., Structure. 7(8):943-52, 1999, abstract only.*
Midoro-Horiuti et al. Ann Allergy Asthma Immunol. 87(4):261-71, 2001, abstract only.*
Mohapatra et al., Curr Allergy Asthma Rep. 5(5):381-7, 2005, abstract only.*
Ipsen et al., Clin Rev Allergy Immunol. 15(4):389-96, 1997, abstract only.*
Roberts et al., Immunology. 76(3):389-96, 1992, abstract only.*
Leduc-Brodard et al., J Allergy Clin Immunol. 98(6 Pt 1): 1065-72, 1996, abstract only.*
Andersson et al., Int Arch Allergy Immunol. 130 (2):87-107, 2003, abstract only.*
Moingeon et al., Int Arch Allergy Immunol. 146(4):338-42. 2008, abstract only.*
http://www.allergen.org/search.php?TaxSource=Plantae+Liliopsida &TaxOrder= Sep. 28, 2010.*
http://www.allergen.org/ Sep. 28, 2010.*
Andersson, K. et al., "Characteristics and Immunobiology of Grass Pollen Allergens," Int. Arch Allergy Immunol, 2003, vol. 130, pp. 87-107.
Dolecek, C. et al., "Molecular characterization of *Phl p* II, a major timothy grass (*Phleum pretense*) pollen allergen," Federation of European Biochemical Societies, Dec. 1993, vol. 335, No. 3, pp. 299-304.

(Continued)

*Primary Examiner* — Nora Rooney
(74) *Attorney, Agent, or Firm* — Millen, White, Zelano & Branigan, P.C.

(57) ABSTRACT

The invention relates to a method for quickly and effectively isolating and purifying five, namely the group 1, 2, 3, 10 and 13 allergens from grass pollen. The purification of said grass pollen is based on the inventive combination of hydrophobic interaction chromatography, gel filtration and cation exchange chromatography. The proteins obtained by the inventive method facilitate an improved diagnosis of pollen allergies and are used in pharmaceutical preparations for the therapy of pollenogenic diseases.

4 Claims, 1 Drawing Sheet

OTHER PUBLICATIONS

Petersen, A. et al., "Phl p 3: Structural and immunological characterization of a major allergen of timothy grass pollen," Clinical and Experimental Allergy, 2006, vol. 36, pp. 840-849.

Petersen, A. et al., "Group 13 grass allergens: Structural variability between different grass species and analysis of proteolytic stability," J. Allergy Clin. Immunol., May 2001, vol. 107, No. 5, pp. 856-862.

Schweimer, K. et al., "Solution structure of Phl p 3, a major allergen from timothy grass pollen," Biol. Chem. Jul. 2008, vol. 389, pp. 919-923.

Suck, R. et al., "Rapid and efficient purification of *Phleum pretense* major allergens Phl p 1 and group Phl p 2/3 using a two-step procedure," Journal of Immunological Methods, 1999, vol. 229, pp. 73-80.

Suck, R. et al., "The high molecular mass allergen fraction of timothy grass pollen (*Phleum pretense*) between 50-60 kDa is comprised of two major allergens: Phl p 4 and Phl p 13," Clinical and Experimental Allergy, 2000, vol. 30, pp. 1395-1402.

Suck, R. et al., "Complementary DNA cloning and expression of a newly recognized high molecular mass allergen Phl p 13 from timothy grass pollen (*Phleum pretense*)," Clinical and Experimental Allergy, 2000, vol. 30, pp. 324-332.

Fahlbusch et al., "Application of reversed-phase high-performance liquid chromatography in the purification of major allergens from grass pollen," Journal of Immunological Methods, Bd. 194, Nr. 1, 1996, 27-34.

Database Chemabs Online! Chemical Abstracts Service, Columbus, Ohio, Bolzacchini et al., "Purification of *Phleum pratense* pollen extract by immunoaffinity chromatography and high-performance ion-exchange chromatography" Database accession No. 115:112253 CA, 1991.

Suck et al., "Rapid and efficient purification on *Phleum pratense* major allergens Ph1 p 1 and group Ph1 p 2/3 using a two-step procedure" Journal of Immunological Methods, Bd. 229, Nov. 1999, 73-80.

Esch, R.E. In Allergens and Allergen Immunotherapy, 3rd edition, 2004, Marcel Dekker, pp. 185-205.

Blumenthal et al. In Allergens and Allergen Immunotherapy, 3rd edition, 2004, Marcel Dekker, pp. 37-50.

Williams, A. "Overview of Conventional Chromatography" in Current Protocols in Protein Science, 1995, John Wiley and Sons, 8.1.1-8.1.9.

Williams et al., "Ion-Exchange Chromatography" in Current Protocols in Protein Science, 1999, John Wiley and Sons, 8.2.1-8.2.30.

Hegel, L. "Gel-Filtration Chromatography" in Current Protocols in Protein Science, 1998, John Wiley and Sons, 8.3.1-8.3.30.

Kennedy, RM, "Hydrophobic-Interaction Chromatography" in Current Protocols in Protein Science, 2000, John Wiley and Sons, 8.4.1-8.4.21.

Bolzacchini et al., "Purification of *Phleum pretense* pollen extract by immunoaffinity chromatography and high-performance ion-exchange chromatography" J Chromatography, 1991, 548:229-234.

\* cited by examiner

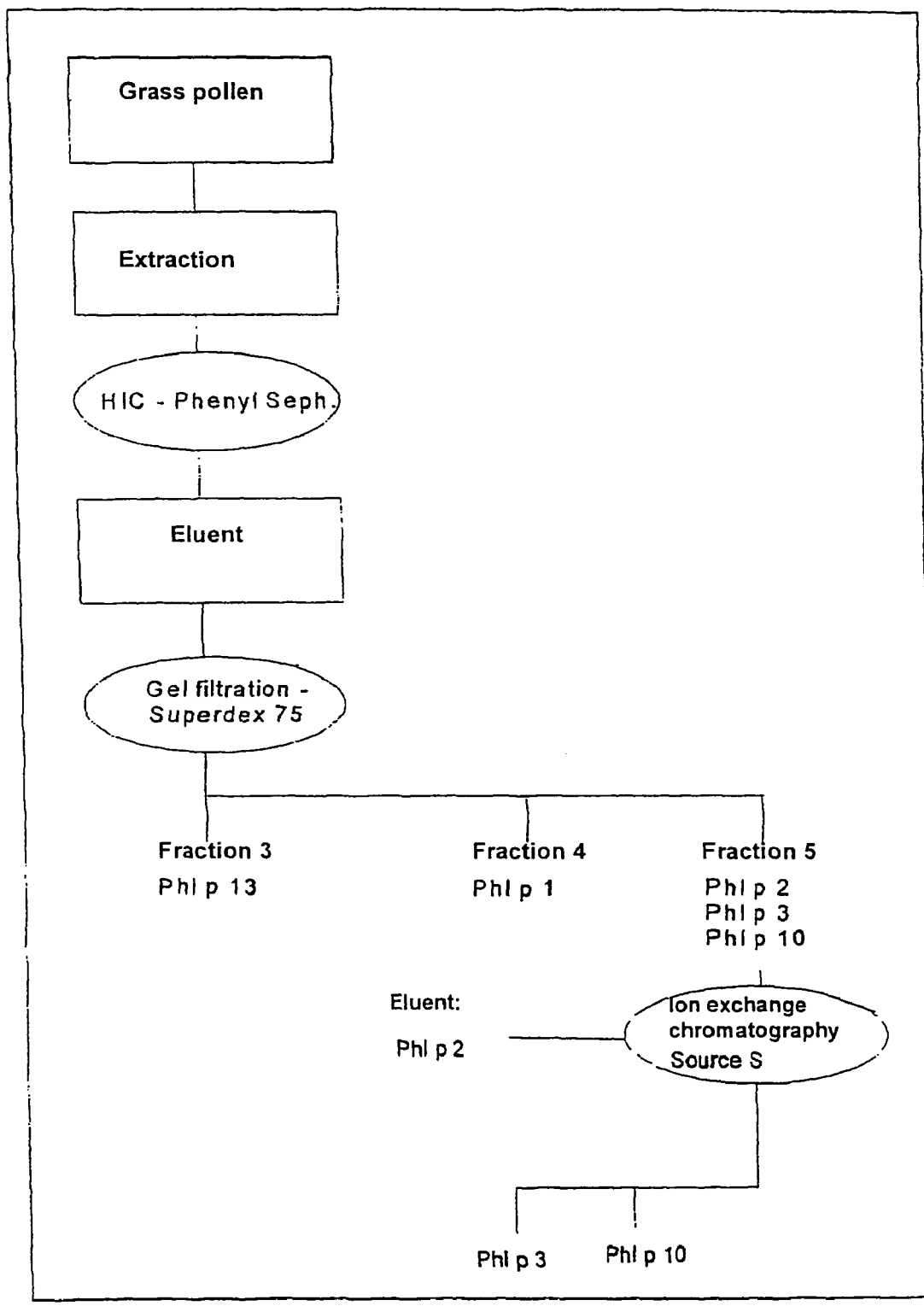

METHOD FOR ISOLATING AND PURIFYING GRASS POLLEN ALLERGENS

This application is a divisional application of U.S. Ser. No. 10/069,285, filed Aug. 8, 2002, which issued as U.S. Pat. No. 7,326,769 on Feb. 5, 2008, which is a national phase application of PCT/EP00/08059, filed Aug. 18, 2000, claiming foreign priority to German Application 19939982.4, filed Aug. 24, 1999, and this application is also related to U.S. Ser. No. 12/000,508 filed on Dec. 13, 2007, which is abandoned and also claimed the benefit of U.S. Ser. No. 10/069,285.

The invention relates to a method for the rapid and effective isolation and purification of five allergens from groups 1, 2, 3, 10 and 13 from grass pollen. The natural raw material used for the allergen purification is the pollen of sweet grasses, such as, for example, of *Phleum pretense*. The purification is based on a novel combination of hydrophobic interaction chromatography, gel filtration and cation exchange chromatography. The proteins obtained in this way can be used for improved diagnostics of pollen allergies and for pharmaceutical preparations for the therapy of pollen-allergy diseases.

Type 1 allergies are of worldwide importance. Up to 20% of the population in industrialised countries suffers from complaints such as allergic rhinitis, conjunctivitis or bronchial asthma, which are caused by allergens present in the air (aeroallergens), which are released by various sources, such as plants, mites, cats or dogs. Up to 40% of these type 1 allergy sufferers in turn exhibit specific IgE reactivity in the case of grass pollen allergens (Freidhoff et al., 1986, J Allergy Clin Immunol 78, 1190-201).

The substances which trigger type 1 allergy are proteins, glycoproteins or polypeptides. After uptake via the mucous membranes, these allergens react with the IgE molecules bonded to the surface of mast cells in sensitised persons. If two or more IgE molecules link up with one another through an allergen, this results in the secretion of mediators (for example histamine, prostaglandins) and cytokines by the effector cell and thus in the corresponding clinical symptoms.

Depending on the relative frequency of the allergy sufferers having IgE antibodies against certain allergens, a distinction is made between major and minor allergens. In the case of timothy grass (*Phleum pratense*), Phl p 1 (Petersen et al., 1993, J. Allergy Clin. Immunol. 92, 789-796), Phl p 5 (Matthiesen and Lowenstein, 1991, Clin. Exp. Allergy 21, 297-307; Petersen et al., 1992), Phl p 6 (Petersen et al., 1995, Int. Arch. Allergy Immunol. 108, 49-54) and Phl p 2/3 (Dolecek et al., 1993) have hitherto been characterised as major allergens and Phl p 4 (Löwenstein, 1978, Prog. Allergy 25, 1-62) and groups 10 and 11 from *Lolium perenne* (Ansari et al., 1987, J. Allergy Clin. Immunol. 80, 229-235) as minor allergens. In addition, a further high-molecular-weight major allergen that has been named Phl p 13 has recently been described. The group 1 and 13 allergens are glycosylated.

In connection with the present invention, allergy groups 1, 2, 3, 10 and 13 are of particular importance. Established purification methods of the natural allergens are based on isolation of individual proteins in each case. By means of affinity chromatography using specific antibodies, group 1 allergens from *Lolium perenne* (Boutin et al., 1996, Int. Arch. Allergy Immunol. 112, 218-225) and *Phleum pratense* (Grobe et al., 1999, Eur. J. Biochem. 263, 33-40), for example, have been purified hitherto. This method is of limited capacity and is carried out using an extreme pH, with the consequence that it is not guaranteed that the native conformation can be obtained. Other methods are based on various multi-stage sequences of chromatographic steps. Individual allergens, such as, for example, group 10 (Ansari et al., 1987, J Allergy Clin Immunol 80, 229-235) or group 3 (Ansari et al., 1989, Biochemistry 28, 8665-8670), are in each case obtained here. Other allergens are lost or cannot be prepared in pure form in these methods.

DNA sequence data are available, inter alia, for Phl p 1 (Laffer et al., 1994, J. Allergy Clin. Immunol. 94, 1190-98; Petersen et al., 1995, J. Allergy Clin. Immunol. 95 (5), 987-994), Phl p 5 (Vrtala et al., 1993, J. Immunol. 151 (9), 4773-4781), Phl p 6 (Petersen et al., 1995, Int. Arch. Allergy Immunol. 108 (1), 55-59) and Phl p 2 (Dolecek et al., 1993, FEBS 335 (3), 299-304). With the aid of cDNA sequences, it is possible to produce recombinant allergens which can be used in diagnostics and therapy (Scheiner and Kraft, 1995, Allergy 50, 384-391).

A classical approach to effective therapeutic treatment of allergies is specific immunotherapy or hyposensitisation (Fiebig, 1995, Allergo J. 4 (6), 336-339; Bousquet et al., 1998, J. Allergy Clin Immunol. 102 (4), 558-562). In these methods, the patient is injected subcutaneously with natural allergen extracts in increasing doses. However, this method entails the risk of allergic reactions or even anaphylactic shock. In order to minimise these risks, innovative preparations in the form of allergoids are employed. These are chemically modified allergen extracts which have significantly reduced IgE reactivity, but identical T-cell reactivity compared with the untreated extract (Fiebig, 1995, Allergo J. 4 (7), 377-382).

A greater degree of therapy optimisation would be possible with highly purified allergens. Defined cocktails from natural allergens are able to supersede the previous extracts since the latter, in addition to the various allergens, contain a relatively large number of immunogenic, but non-allergenic accompanying proteins which are not necessary for the specific immunotherapy. The use of allergen cocktails also enables the preparation of patient-specific allergen mixtures corresponding to the sensitisation spectrum. Realistic perspectives which could result in safe hyposensitisation with high-purity natural allergens are offered by modified allergens in which IgE epitopes are destroyed by irreversible modification of the secondary and tertiary structure without impairing the T-cell epitopes which are essential for the therapy.

The invention can likewise advantageously be used in in-vitro and in-vivo diagnostics of allergic illnesses, especially of pollinosis. To this end, the purified allergen groups are employed in established methods for the detection of IgE antibodies.

The invention relates to a biochemical purification method which results in the isolation of 4 major allergens and 1 minor allergen from aqueous shorttime pollen extracts by an efficient three-stage purification. The natural raw material used is pollen of the Graminae, such as, for example, *Phleum pretense, Lolium perenne, Dactylis glomerata, Poa pratensis, Cynodon dactylon, Holcus lanatus*, inter alia. FIG. 1 shows the purification scheme of the 5 allergens mentioned from grass pollen extracts. The allergen names Phl p 1 to Phl p 13 correspond to the names allergens 1 to 13 otherwise used in the text.

The invention thus relates to a method for isolating essentially pure group 1, 2, 3, 10 and 13 grass allergens in which an aqueous extract of Graminae pollen is prepared from, and the soluble constituents are subjected to hydrophobic interaction chromatography, a gel filtration step and, if desired, cation exchanger chromatography.

In accordance with the invention, it is also possible to carry out a plurality of steps of one type of chromatography, but in general the method is so effective that one separation step is sufficient in each case.

The method is particularly suitable for isolating said allergens from the pollen of the species *Phleum pratense, Lolium perenne, Dactylis glomerata, Festuca pratensis, Holcus lanatus, Poa pratensis, Secale cereale*.

In a preferred embodiment, the extraction is carried out by means of tris/HCl-buffered aqueous solution. However, it is also possible to employ, in accordance with the invention, other known aqueous buffer solutions.

For the purification of the said allergens, the soluble constituents of the extract are employed. To this end, the extract is centrifuged for from 3 to 8 minutes, preferably 5 minutes, at from 18,000 to 30,000×g, and the supernatant is taken for further purification. Alternatively, the insoluble constituents can be separated off by other methods, for example by filtration.

The first chromatographic purification step is carried out by means of hydrophobic interaction chromatography, for example on Sepharose®. In this, a large number of impurities are immobilised on the support, while the desired allergens are located in the fraction passing through the column. Corresponding other support materials can likewise be employed.

The invention thus relates to a corresponding method in which the group 1, 2, 3, 10 and 13 grass allergens are separated off from other constituents by means of hydrophobic interaction chromatography.

In the subsequent purification step, the grass allergens are separated into three fractions, with groups 1 and 13 each representing one fraction and groups 2, 3 and 10 representing the third fraction. The invention thus relates in particular to a method in which the group 1 and 13 allergens are obtained in separate fractions by a subsequent gel filtration step and are separated off from the group 2, 3 and 10 allergens.

The latter can then be separated from one another in accordance with the invention by a subsequent chromatography step via a cation exchanger.

The invention therefore relates to a method in which the group 2, 3 and 10 allergens obtained after the gel filtration step are separated from one another by subsequent cation exchange chromatography.

The said allergens, which are known per se, are identified either via their known, different physical, chemical, biological or immunological properties, in particular by means of isoelectric focusing, UV absorption measurements, SDS-PAGE and specific antibodies. These methods and techniques are known and have been described in general terms.

The yield of the allergens obtained in accordance with the invention is 0.5-1.5%, based on the originally employed total protein of the grass pollen.

The invention also serves to improve in-vivo and in-vitro diagnostics as part of identification of the patient-specific sensitisation spectrum which resolves allergen components. The invention thus relates to methods for the in-vivo and in-vitro diagnosis of pollen allergies using the allergens obtained in accordance with claims 1 to 6.

The invention-likewise serves to prepare improved-preparations for specific immunotherapy of grass pollen allergies, which is achieved by separating off extract constituents which are immunogenic, but are irrelevant for the therapy. It is furthermore possible, through chemical reaction of the purified allergens, to obtain an allergoid preparation. The invention thus also relates is to a pharmaceutical preparation which comprises one or more allergens obtained by the method according to the invention and, if desired, corresponding assistants and excipients.

The method is described in detail below:

The purification of the natural allergens from timothy grass pollen is carried out in a three-step process (see FIG. 1). After aqueous extraction with tris/HCl-buffered solution (20 mM tris/HCl, 1 mM EDTA, pH 8.0) of pollen for 30 minutes, the extract is separated by centrifugation, preferably at 20,000×g for five minutes. The tris/HCl-buffered (20 mM tris/HCl, 1 mM EDTA, pH 8.0) supernatant is treated with 1 M ammonium sulfate and subsequently subjected to hydrophobic interaction chromatography (Phenyl-Sepharose High Performance, Pharmacia). A typical column is packed with from 50 to 100 ml of the support material and operated at a flow rate of about 5 ml/min. The fraction passing through the column comprises exclusively the proteins of five allergen groups: group 1 (30-35 kDa), group 2 (11 kDa), group 3 (12 kDa), group 10 (13 kDa) and group 13 (55-60 kDa). This is followed by a reduction in the volume, preferably by ultrafiltration or lyophilisation.

In a second step, the group 13 and 1 allergens are then separated from the low-molecular-weight allergens by gel filtration in accordance with their different molecular weights using Superdex® 75 prep grade (Pharmacia) or similar known support materials which are suitable for this purpose. The elution medium is preferably 50 mM ammonium hydrogencarbonate. The column is operated at a flow rate of about 5 ml/min. Three fractions are obtained which comprise allergens 1 and 13 (each separately) and 2, 3 and 10 (in one fraction).

The low-molecular-weight group 2, 3 and 10 allergens, which were eluted together in the third fraction of the gel filtration, are separated from one another by means of cation exchange chromatography. To this end, the lyophilised sample is taken up in an aqueous buffer, preferably 20 mM phosphate buffer, pH 7.2, and applied to a cation exchanger column equilibrated with this buffer (for example Source S®). The fraction passing through the column contains the acidic allergen 2. The bound allergens 3 and 10 are eluted one after the other over about 20 column volumes by means of a salt gradient from 0 to 500 mM NaCl. The low-molecular-weight allergen group is thus separated into its individual allergens. Other cation exchanger materials can also be employed in accordance with the invention.

By means of the method according to the invention that is provided and which is distinguished by the specific sequence of the chromatography steps and the choice of chromatography media, the present invention thus facilitates a highly scalable production method for the isolation of a plurality of high-purity, natural grass allergens which is not labour-intensive or time-consuming and which can be implemented technologically. Since the purification methods used are very gentle for proteins, their conformations and antigeneity are retained. This is a prerequisite for successful diagnostics of allergic illnesses.

BRIEF DESCRIPTION OF DRAWINGS

FIG. 1: Illustrates the purification of the natural allergens from timothy grass pollen in a three-step process.

The invention claimed is:

1. A pharmaceutical composition comprising a carrier and purified group 1, 2 and 13 grass allergen, which allergens were purified by a method comprising preparing an aqueous extract of *Phleum pratense* Gramineae pollen and subjecting the extract to hydrophobic interaction chromatography, followed by gel filtration, and polling the purified group 1, 2 and 13 grass allergens into the pharmaceutical composition.

2. A pharmaceutical composition according to claim 1, wherein the extraction is carried out by Tris/HCl-buffered aqueous solution.

3. A pharmaceutical composition according to claim 1, wherein the group 1 and 13 allergens are obtained in separate fractions by a filtration step and are separated from the group 2 allergen.

4. A pharmaceutical composition according to claim 1, wherein the gel filtration is followed by cation exchange chromatography.

* * * * *